(12) United States Patent
Wada

(10) Patent No.: US 8,562,134 B2
(45) Date of Patent: Oct. 22, 2013

(54) VISION SHIFT AMOUNT MEASURING METHOD AND VISION SHIFT AMOUNT MEASURING JIG

(75) Inventor: Osamu Wada, Ina (JP)

(73) Assignee: Hoya Lens Manufacturing Philippines Inc., Cavite (PH)

( * ) Notice: Subject to any disclaimer, the term of this patent is extended or adjusted under 35 U.S.C. 154(b) by 274 days.

(21) Appl. No.: 12/971,396

(22) Filed: Dec. 17, 2010

(65) Prior Publication Data

US 2011/0157549 A1 Jun. 30, 2011

(30) Foreign Application Priority Data

Dec. 29, 2009 (JP) ................................ 2009-299058

(51) Int. Cl.
- *A61B 3/10* (2006.01)
- *A61B 3/02* (2006.01)
- *G02C 5/00* (2006.01)
- *G06K 9/20* (2006.01)
- *G01B 1/00* (2006.01)

(52) U.S. Cl.
USPC ............. 351/204; 351/41; 351/222; 382/282; 33/200; 33/507

(58) Field of Classification Search
USPC ........... 351/204, 200, 205, 222, 246, 41, 159, 351/177, 178; 382/282; 33/507, 200
See application file for complete search history.

(56) References Cited

U.S. PATENT DOCUMENTS

| | | | | |
|---|---|---|---|---|
| 1,981,438 | A | * | 11/1934 | Smith ........................... 351/228 |
| 5,754,272 | A | * | 5/1998 | Dimalanta .................... 351/204 |
| 6,827,443 | B2 | | 12/2004 | Fisher et al. .................. 351/209 |
| 8,115,792 | B2 | * | 2/2012 | Petsch et al. .................. 347/224 |
| 2007/0222938 | A1 | * | 9/2007 | Meyers .......................... 351/41 |

FOREIGN PATENT DOCUMENTS

| | | |
|---|---|---|
| JP | 06-063015 | 3/1994 |
| JP | 2003-523244 | 8/2003 |
| JP | 2006-091411 | 4/2006 |
| JP | 2008-521027 | 6/2008 |
| WO | WO 2006/054985 A1 | 5/2006 |

\* cited by examiner

*Primary Examiner* — Dawayne A Pinkney

(74) *Attorney, Agent, or Firm* — DLA Piper LLP (US)

(57) ABSTRACT

A vision shift amount measuring method includes: forming a reference mark indicating a distance eye point on a surface of a spectacle lens attached to a spectacle frame practically worn by a wearer, and forming a plurality of opaque lines in an area expected to contain a shifted vision on the surface of the spectacle lens with a predetermined space between the adjoining lines; and allowing the wearer wearing the spectacle frame to select the line closest to a position through which the vision passes from the plural formed lines.

12 Claims, 11 Drawing Sheets

VISION SHIFT AMOUNT MEASURING METHOD AND VISION SHIFT AMOUNT MEASURING JIG

BACKGROUND

1. Technical Field

The present invention relates to a vision shift amount measuring method and a vision shift amount measuring jig used for spectacle lenses.

2. Related Art

When viewing an object, a person rotates his/her head or eyes for obtaining side view and upper and lower view (hereinafter referred to as viewing action), The rotation angles of the head and eyes during the viewing action are different for each person, and thus various types of spectacle lens designing method and adjusting method capable of dealing with the viewing action of each person have been proposed (for example, see JP-T-2003-523244 and JP-T-2008-521027).

For designing spectacle lenses suitable for each person, measuring a vision shift amount of the person is essential. The vision shift amount herein refers to a distance of vision shift of a wearer of spectacles on a lens, defined as a concept which includes an eyeball downward movement amount corresponding to a distance of vision shift on the lens when the wearer of the spectacles shifts vision in the up-down direction to change the viewing condition from horizontal view to near view (to the condition of reading a book, for example), and a side view amount corresponding to a distance of vision shift on the lens when the wearer of the spectacles shifts vision in the left-right direction to change the viewing condition from horizontal view to side view.

In designing a progressive-power lens, the eyeball downward movement amount is particularly important. The progressive-power lens is an aspherical lens which includes a distance portion having a power (dioptric power) corresponding to distant view, and a near portion having power corresponding to near view. The distance portion is located in an upper area of the lens, and the near portion is located in a lower area of the lens. A progressive band whose power progressively changes is further provided between the distance portion and the near portion. These portions and band have no boundary between one another, and a wearer of the progressive-power lens can view objects located in a distant place and in a near place through a single lens. The distance portion, the near portion, and the progressive band are required to be adjusted according to the purpose of use for each person (for distant-near view use, middle-near view use, near-near view use, full-time use, part-time use, still use, dynamic use and other purposes) (optical fitting). The eyeball downward movement amount is measured as a distance between a distance eye point as the vision position of the wearer of the spectacles on the lens in the horizontal view condition and a near eye point as the vision position of the wearer on the lens in the near view condition.

Various methods for detecting the distance eye point and the near eye point have been proposed (for example, see JP-A-2006-91411). According to JP-A-2006-91411, a group of light-transmissive color bars having two or more different colors disposed adjacent to each other are provided on each of detection areas for the distance eye point and the near eye point of a transparent plate body attachable to a wearing frame or a spectacle lens. For detecting the eye points, the wearer views direct light or reflection light emitted from a pen-type light or the like, and recognizes the position of the light passing through the detection areas.

According to JP-T-2003-523244 and JP-T-2008-521027, quantitative values are obtained by using a head and eyeball movement measuring device such that a lens optimized for each person can be produced based on the obtained values. However, in determining the near eye point on the progressive-power lens, the posture of the wearer is a factor largely concerned with the determination as well as the head and eyeball movements, Thus, it is difficult in some cases to determine the near eye point with high accuracy by the method of these references.

Moreover, the measurement of the eyeball movement disclosed in JP-T-2003-523244 and JP-T-2008-521027 requires a long time of detection which imposes a too much detection burden on a customer, and also requires a highly expensive detection device to be prepared.

On the other hand, when the group of light-transmissive color bars are viewed at a distance of 12 mm before the eyes in the method disclosed in JP-A-2006-91411, modulated colors are recognized (mixed colors or lighter colors) due to the effect of out-of-focus condition or diffraction. In this case, it is difficult in some cases to securely determine the color differences (lowering of visual recognizability).

In addition, the operation for detecting both the distance eye point and the near eye point and calculating the difference between the relative positions of these points is a complicated process, which lowers accuracy in some cases and prevents practical use of the method.

SUMMARY

An advantage of some aspects of the invention is to provide a vision shift amount measuring method and a vision shift amount measuring jig capable of measuring a vision shift amount easily and accurately at low cost.

A vision shift amount measuring method according to an aspect of the invention includes: forming a reference mark indicating a distance eye point on a surface of a spectacle lens attached to a spectacle frame practically worn by a wearer, and forming a plurality of opaque lines in an area expected to contain a shifted vision on the surface of the spectacle lens with a predetermined space between the adjoining lines; and allowing the wearer wearing the spectacle frame to select the line closest to a position through which the vision passes from the plural formed lines.

The vision shift amount herein is a concept which represents a shift distance of the vision of the wearer of the spectacle on the lens, and includes both an eyeball downward movement amount corresponding to the shift distance of the vision on the lens when the wearer of the spectacle shifts the vision in the up-down direction for changing the vision from the condition of the horizontal view to the condition of the near view (such as a condition of reading a book), and a side view amount corresponding to the shift distance of the vision on the lens when the wearer of the spectacle shifts the vision in the left-right direction for changing the condition of the horizontal view to the side view. The side view amount includes an eyeball outward movement amount produced when the outside of the lens is viewed and an eyeball inward movement amount produced when the inside of the lens is viewed.

The definition of the spectacle lens includes a dummy lens having no power as well as a spectacle lens having power to be practically used by the wearer.

According to this aspect of the invention, the reference mark indicating the distance eye point and the plural lines formed in the area expected to contain the shifted vision are formed on the surface of the spectacle lens. The distance eye point is the position on the spectacle lens through which position the vision passes in the horizontal view of the wearer wearing the spectacle. The position of the distance eye point is easily measured and thus determined beforehand. The plural lines are positioned on the lower part or the side part of the spectacle lens, for example. The wearer practically wears the spectacle lens on which the reference mark and the plural lines (hereinafter only referred to as marks as well as a concept including both the reference mark and the plural lines) are formed, and determines the line coinciding with the shifted vision. This determination is made based on whether the vision agrees with the line or which line is the closest to the vision. Thus, the vision shift amount can be obtained by selecting the recognizable line from the plural lines when viewing an object while shifting the vision and calculating the distance between the position of the determined line and the distance eye point established in advance.

According to this method, the position of the vision on the spectacle lens is determined by using the spectacle frame practically worn by the wearer. Thus, not only the viewing action (movements of eyes and head) of the wearer but also the posture and habit of the wearer when viewing an object are considered for the measurement. Accordingly, the accuracy of the measurement increases.

In addition, the measurement requires only determination of the degree of agreement between the shifted vision and any one of the plural lines on the spectacle lens. Thus, the measurement can be easily carried out at low cost without imposing a burden on the wearer.

The plural lines are opaque lines. Concerning the degree of opaqueness, the total light transmittance is preferably 50% or lower, more preferably 30% or lower, and further preferably 20% or lower. The wearer can recognize the colors of the lines by reflection light produced from light entering from the back and reflected by the opaque lines. When viewing an object, the wearer practically wearing the spectacle sees the blurred lines on the spectacle lens. In this case, the visibility of the colors lowers. According to this aspect of the invention, however, the rate of reflection light reflected by the opaque color lines increases, and therefore the wearer can securely determine the color difference by the increased amount of light entering the eyes (improvement of visibility). Thus, the wearer can easily determine the color in the measurement of the vision shift amount.

The plural lines are disposed with the predetermined space between the adjoining lines. In this case, the space between the lines has light-transmissibity, allowing the object to be viewed through the space. Thus, the wearer can visually recognize the object through the space between the lines, which allows the measurement to be performed in a more natural condition for visual recognition, and increases the measurement accuracy.

The distance eye point which can be easily measured is determined for each person in advance, and the reference mark is formed at this position. Also, the plural lines are formed in the area expected to contain the shifted vision, and the wearer is only required to determine the line coinciding with the vision on the spectacle lens According to this method, the distance eye point is fixed, and the position of the vision after the vision shift is only determined. That is, the vision downward movement amount is calculated from the absolute position. Accordingly, the measurement can be performed highly accurately by easy operation, This aspect of the invention may be either used for measuring the vision shift amount prior to the lens design or for checking whether the lens produced after the lens design is appropriate for the wearer. In the former case, the measurement is executed by using a dummy lens made of acrylic resin and having no power.

According to the vision shift amount measuring method of the aspect of the invention, it is preferable that the plural lines are disposed such that the distance between the centers of the adjoining lines lies in the range from 1.5 mm to 2.5 mm.

When the distance between the centers of the adjoining lines is shorter than 1.5 mm, there is a possibility that the wearer cannot visually recognize an object between the lines. When the distance between the centers of the adjoining lines exceeds 2.5 mm, the number of the lines formed on the spectacle lens decreases. In this case, the accuracy of the measurement lowers to such a level that the practical use of the method is difficult. When the plural lines are disposed at the positions within the range described above, the wearer can easily determine the color. As a result, the accuracy of the measurement increases.

According to the vision shift amount measuring method of the aspect of the invention, it is preferable that each width of the lines lies in the range from 0.1 mm to 1.5 mm.

The diameter of a human pupil lies approximately in the range from 2 mm to 8 mm. According to this method, each width of the lines is 1.5 mm or smaller. In this case, the visibility is not completely blocked, and the object can be visually recognized through the space between the lines. When the width of the line exceeds 1.5 mm and becomes equivalent or larger than the pupil diameter, there is a possibility that accurate measurement cannot be achieved due to complete blocking of the visibility. When the width of the line is smaller than 0.1 mm, the excessively narrow line lowers its visual recognizaibility and makes color determination difficult in some cases. When the width of the line lies within the range described above, the wearer can easily determine the color, which facilitates execution of the measurement. It is more preferable that each width of the lines lies within the range from 0.5 mm to 1.2 mm.

Each width of the lines and each distance between the centers of the adjoining lines are set at appropriate values such that the predetermined distance can be produced between the adjoining lines. When each width of the line and each distance between the centers of the adjoining lines are both set at 1.5 mm, for example, no space is produced between the adjoining lines. In this case, the width of the line is decreased, or the distance between the center lines is increased.

According to the vision shift amount measuring method of the aspect of the invention, it is preferable that at least the adjoining lines of the plural lines have colors different from each other.

According to this method, the adjoining lines have different colors. In this case, the wearer is only required to answer the recognized color during the measurement. Thus, the wearer can determine the line intuitively, which reduces the burden on the wearer.

According to the vision shift amount measuring method of the aspect of the invention, it is preferable that the plural lines are formed in an area expected to contain a near eye point on the surface of the spectacle lens and are disposed in parallel with a horizontal visible field which passes through the distance eye point and extends in the horizontal direction.

According to this method, the position of the near eye point can be determined. More specifically, the plural lines are formed on the area expected to contain the near eye point. Since the plural lines are formed in parallel with the horizontal direction, the distance between the distance eye point and these lines corresponds to the eyeball downward movement amount. In this case, the wearer can establish the position of the near eye point only by determining the color of the line recognizable in the near view. Thus, the measurement can be easily performed without imposing a burden on the wearer.

According to the vision shift amount measuring method of the aspect of the invention, it is preferable that the plural lines are formed in an area expected to contain one end of a horizontal visible field which passes through the distance eye point and extends in the horizontal direction, and are disposed in the direction crossing the horizontal visible field at right angles.

According to this method, the wearer determines the line closest to the vision which contacts the plural lines formed at one end of the horizontal visible field after changing from the condition of the horizontal view to the condition of viewing the left or the right. Since the plural opaque lines have high visual recognizability for the wearer, the wearer can easily determine the line. The side shift amount appropriate for the wearer can be easily measured based on the distance between the line determined by this method and the distance eye point.

Moreover, the measurement is performed by using the spectacle frame practically worn by the wearer. Thus, not only the viewing action of the wearer (movements of eyes and head) but also the posture and habit of the wearer are considered in measurement, which increases the accuracy of the measurement.

According to the vision shift amount measuring method of the aspect of the invention, it is preferable that the reference mark and the plural lines are formed by directly applying ink to the spectacle lens using a stamp.

According to this method, the marks can be easily formed on the surface of the spectacle lens only by pressing the stamp against the surface of the spectacle lens. When projections in a predetermined pattern are provided on the stamp, the stamp can be repeatedly used. In this case, the necessity for preparing a special device or the like is eliminated. Moreover, ink used for the stamp can be directly applied to the surface of the spectacle lens. Thus, the necessity for performing complicated processes prior to measurement is eliminated. Accordingly, the marks can be easily formed on the surface of the spectacle lens at low cost by using the stamp.

According to the vision shift amount measuring method of the aspect of the invention, it is preferable that the reference mark and the plural lines are formed by directly applying ink to the spectacle lens using an ink jet.

According to this method, ink jet is used for forming the marks on the surface of the spectacle lens. In case of the method of ink jet, fine patterns can be easily produced. Thus, the patterns of desired shapes can be easily formed without requiring heavy labor. Moreover, the method of ink jet can directly apply ink to the surface of the spectacle lens, which eliminates the necessity for performing complicated processes before the measurement. Furthermore, the ink applied to the spectacle lens can be easily and completely removed therefrom. In this case, the spectacle lens to be practically used by the wearer (spectacle lens after lens design), on which lens the marks have been directly formed for the use of training, can be employed for daily use after removal of the ink. Thus, the spectacle lens achieves high flexibility in use.

According to the vision shift amount measuring method of the aspect of the invention, it is preferable that the reference mark and the plural lines are formed by producing the reference mark and the plural lines on a surface of a tape capable of adhering to the surface of the spectacle lens, and affixing the tape to the surface of the spectacle lens attached to the spectacle frame practically worn by the wearer with alignment between the distance eye point of the spectacle lens and the reference mark formed on the tape.

According to this method, the reference mark and the plural lines are formed on the surface of the tape in the step of forming the marks, and the tape is affixed to the surface of the spectacle lens.

In this case, it is only necessary to remove the tape at the time of removing the reference mark and the plural lines from the spectacle lens. In case of the method which uses ink adhering to the spectacle lens, the ink is limited to the types which can be easily wiped off. According to the method of the aspect of the invention, however, ink does not adhere to the spectacle lens. Thus, there is no limitation to the type of ink to be used.

A vision shift amount measuring jig according to another aspect of the invention includes: a spectacle holding stand that holds a spectacle having a spectacle frame to which a spectacle lens is attached. A lens carrying unit which contains low-repulsive material provided at a position corresponding to the spectacle lens, and a stamp forming unit which contains convex projections disposed at positions corresponding to a reference mark indicating a distance eye point and a plurality of opaque lines provided in an area expected to contain a shifted vision on the surface of the spectacle lens with a predetermined space between the adjoining lines are provided on the upper surface of the spectacle holding stand.

According to this aspect of the invention, the stamp unit is provided on the lens carrying unit on the upper surface of the spectacle holding stand. Thus, the marks can be easily formed on the surface of the spectacle lens only by pressing the spectacle lens against the lens carrying unit. Particularly, the lens carrying stand is made of low-repulsive material. Thus, the projections of the stamp forming unit closely contact the surface of the spectacle lens when the spectacle lens is pressed against the lens carrying unit. Thus, ink can securely adhere to the surface of the spectacle lens.

Accordingly, even a person in a shop or the like who does not have special techniques can easily form the reference mark and the plural lines on the surface of the spectacle lens, and can easily perform the measurement.

According to the vision shift amount measuring jig of the aspect of the invention, it is preferable that the projection corresponding to the reference mark is provided in such a manner as to freely move in the horizontal direction of the spectacle lens.

According to this structure, the adjustment of the distance eye point in the horizontal direction (left-right direction) can be easily conducted by shifting the projection corresponding to the reference mark. The distance eye point on the spectacle lens differs for each wearer, and the alignment between the distance eye point on the spectacle lens and the distance eye point on the stamp unit in the horizontal direction can be easily carried out at the time of forming the marks on the spectacle lens. Thus, even a person in a shop or the like who does not have special techniques can easily perform the measurement.

According to the vision shift amount measuring jig of the aspect of the invention, it is preferable that the vision shift amount measuring jig further includes a frame supporting member attached in such a manner as to freely move in the direction crossing the horizontal direction of the spectacle lens at right angles to support the spectacle frame.

According to this structure, the adjustment of the spectacle frame (spectacle) in the direction crossing the horizontal direction at right angles (up-down direction) can be easily conducted by shifting the frame supporting member.

The distance eye point on the spectacle lens differs for each wearer, and the alignment between the distance eye point on the spectacle lens and the distance eye point on the stamp unit in the up-down direction can be easily carried out at the time of forming the marks on the spectacle lens . Thus, even a person in a shop or the like who does not have special techniques can easily perform the measurement.

BRIEF DESCRIPTION OF THE DRAWINGS

The invention will be described with reference to the accompanying drawings, wherein like numbers reference like elements.

FIGS. 7A and 7B illustrate a structure of a vision shift amount measuring jig according to the first embodiment, wherein: FIG. 7A is a plan view showing the general structure; and FIG. 7B is a front view showing the general structure.

FIGS. 8A through 8C illustrate conditions of measuring the vision shift amount according to the first embodiment, wherein: FIG. 8A shows a condition of distant view; FIG. 8B shows a condition of near view; and FIG. 8C shows a condition of side view.

FIGS. 9A and 9B illustrates a structure of a vision shift amount measuring jig using a vision shift amount measuring method according to a second embodiment of the invention, wherein: FIG. 9A is a plan view showing the general structure; and FIG. 9B is a front view showing the general structure.

FIGS. 13A and 13B are plan views illustrating marks formed on a spectacle lens according to modified examples of the invention, wherein: FIG. 13A shows a blind provided on a progressive band; and FIG. 13B shows blinds provided on side areas.

DESCRIPTION OF EXEMPLARY EMBODIMENTS

Exemplary embodiments according to the invention are hereinafter described with reference to the drawings. In the respective embodiments, the vertical direction of spectacles worn by a wearer corresponds to the up-down direction of spectacle lenses, and the horizontal direction of the spectacles worn by the wearer corresponds to the left-right direction of the spectacle lenses.

1. First Embodiment

In a first embodiment, a method of measuring a vision shift amount by using spectacles which have dummy lenses made of acrylic resin and attached to a spectacle frame practically worn by a wearer of spectacles will be discussed.

1-1. Dummy Lens

Figure 1:
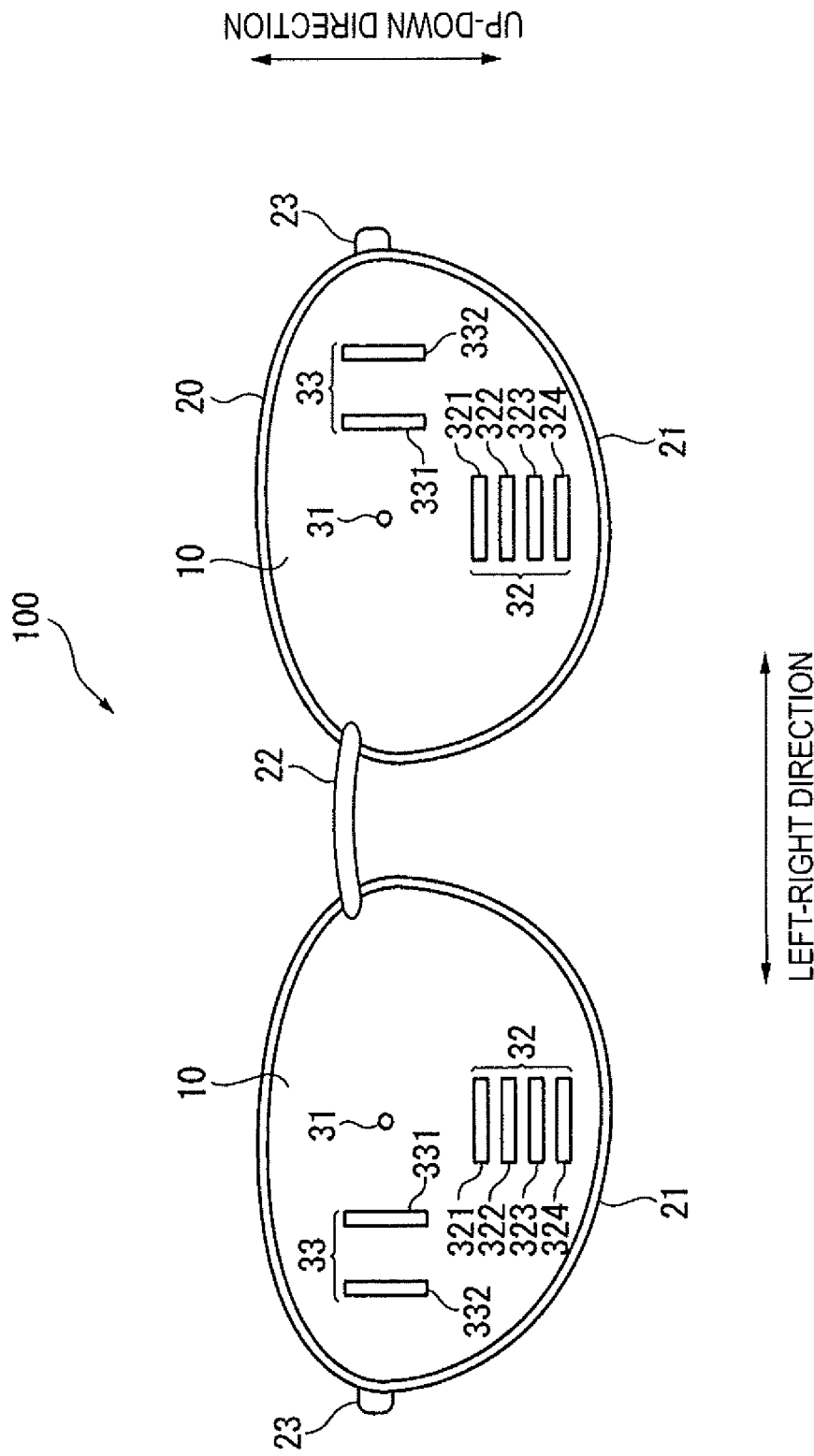
FIG. 1 is a plan view illustrating a condition in which marks are formed on dummy lenses by a vision shift amount measuring method according to a first embodiment of the invention.

As illustrated in FIG. 1, dummy lenses 10 formed by molding are attached to a spectacle frame 20 to constitute spectacles 100.

The spectacle frame 20 has frames 21 each of which surrounds the corresponding dummy lens 10 attached to the frame 21 to form a frame shape, a bridge 22 connecting the left and right frames 21, and temples 23 each of which is attached to the corresponding frame 21 via a hinge in such a manner as to be rotatable.

Marks provided on the surfaces of the dummy lenses 10 are now explained.

Figure 2:
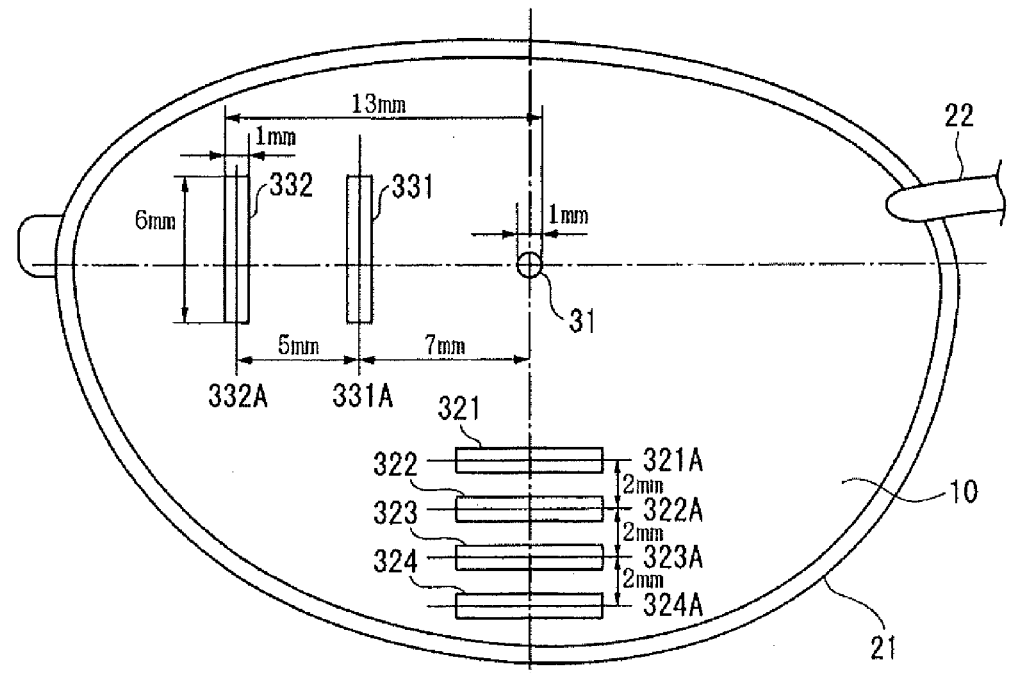
FIG. 2 is a plan view illustrating the enlarged marks according to the first embodiment.

As illustrated in FIGS. 1 and 2, each of the dummy lenses 10 has a reference mark 31 indicating a distance eye point, a first determination mark 32 formed in an area expected to contain a near eye point, and a second determination mark 33 formed in an area expected to contain an outside end of a horizontal visible field (the range of direct view by movement of the eye with the head fixed) which passes through the distance eye point and extends in the horizontal direction.

The reference mark 31 is a circular mark having a diameter of 1 mm as a mark for indicating the position of the distance eye point. The distance eye point is a position through which the vision passes when the wearer practically wearing the spectacles 100 has horizontal view, as the point determined in advance.

The first determination mark 32 is formed in the area expected to contain the near eye point, and is constituted by a plurality of parallel lines extending in the left-right direction of the spectacles 100. These plural lines are opaque lines having different colors, and are disposed such that each clearance between the adjoining lines has a predetermined length. In the explanation of this embodiment, the plural lines are defined as color bars.

More specifically, four color bars of a first color bar 321 (black), a second color bar 322 (green), a third color bar 323 (red), a fourth color bar 324 (blue) are provided in parallel with each other in this order from the distance eye point side. Each of the color bars has an equal width of 1 mm. Assuming that the center lines of the respective color bars in the width direction are a first center line 321A, a second center line 322A, a third center line 323A, and a fourth center line 324A, the color bars are disposed such that each distance between the adjoining center lines of the center lines 321A through 324A becomes 2 mm (see FIG. 2).

The second determination mark 33 is formed in the area expected to contain the outside end of the horizontal visible field on the dummy lens 10, and is constituted by a plurality of parallel lines extending in the up-down direction of the spectacle lens 100. These plural lines are opaque lines having different colors, and are disposed such that each clearance between the adjoining lines has a predetermined length. More specifically, two color bars of a fifth color bar 331 (black) and a sixth color bar 332 (red) are disposed in parallel with each other in this order from the distance eye point side. Each of the color bars 331 and 332 has a width of 1 mm and a length of 6 mm. Assuming that the center lines of the respective color bars in the width direction are a fifth center line 331A and a sixth center line 332A, the color bars are disposed such that the distance between the center position of a distance eye point EP and the fifth center line 331A is 7 mm, and that the distance between the fifth center line 331A and the sixth center line 332A is 5 mm.

The principle of measuring the vision shift amount by using the color bar groups described above is now explained.

Figure 3:
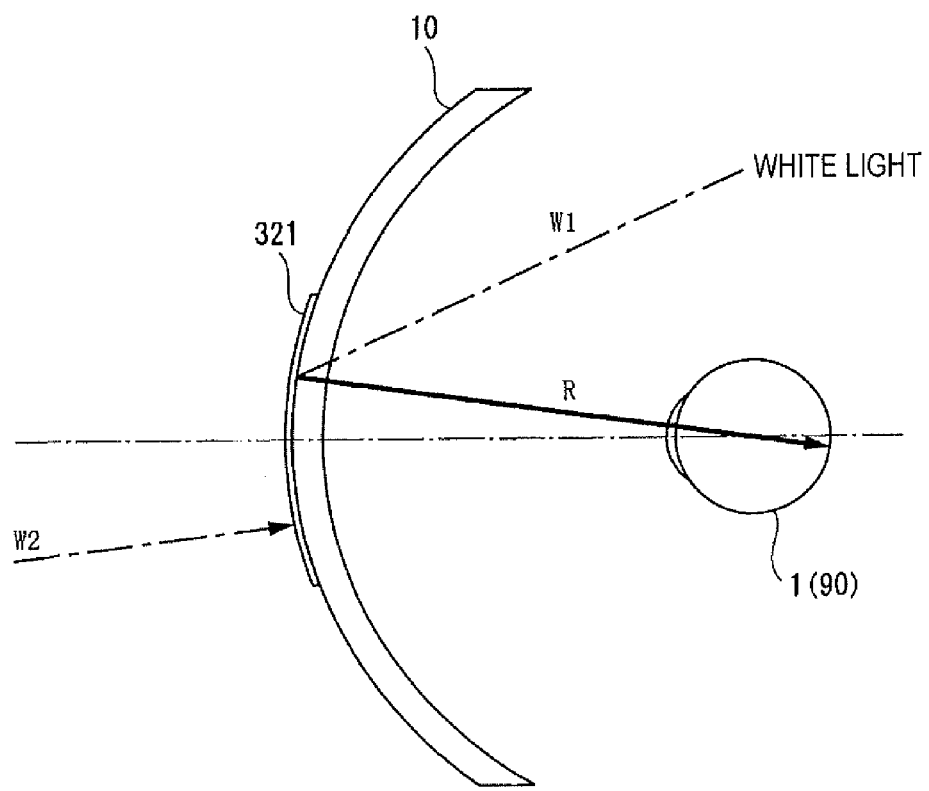
FIG. 3 illustrates a principle of measuring the vision shift amount by using opaque color bars according to the first embodiment.

The color bars having opaque colors have low light-transmissivity. As illustrated in FIG. 3, a wearer 1 (eyeball 90) views reflection light R produced from white light W1 entering from the back and reflected by the opaque first color bar 321. As a result, the wearer 1 recognizes the color of the first color bar 321. White light W2 entering from the front of the wearer 1 is blocked by the opaque first color bar 321. The total light transmittance of each color bar as its light transmissivity is preferably 50% or lower, more preferably 30% or lower, further preferably 20% or lower, and the most preferably 0%. The light transmissivity can be measured by using a measuring device generally used. When the total light transmittance exceeds 50%, the intensity of the reflection light R decreases. In this case, the color of the color bar is difficult to be recognized.

Figure 4:
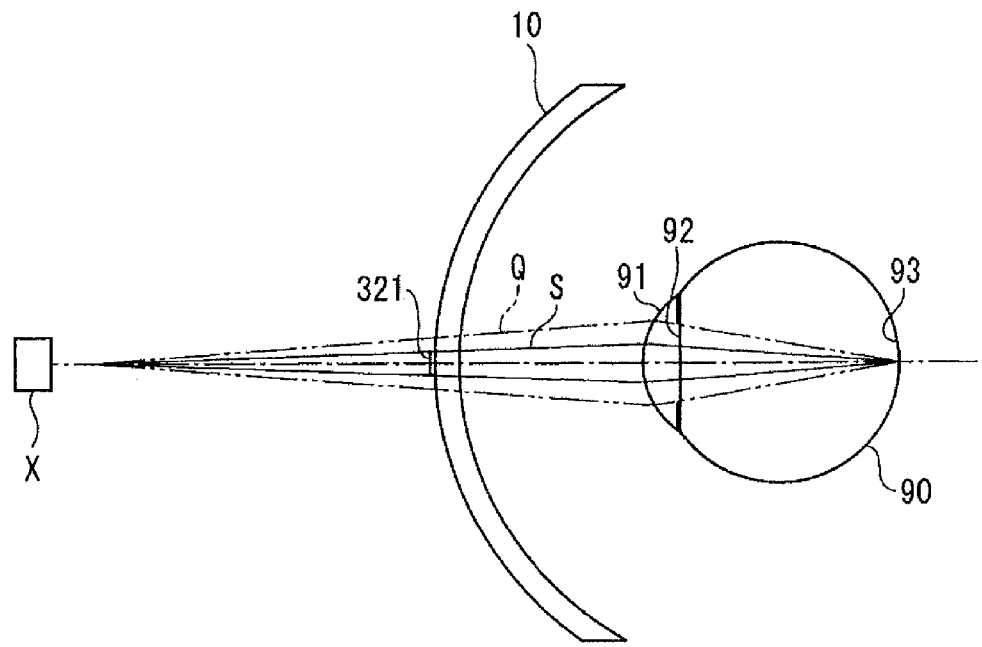
FIG. 4 illustrates a principle of measuring the vision shift amount under a condition in which visibility is partially blocked according to the first embodiment.

FIG. 4 schematically illustrates the eyeball viewing an object. As can be seen from FIG. 4, the eyeball 90 recognizes an object X by formation of an image of light passing through a cornea 91 and a pupil 92 on a retina 93. Since the light coming from the outside is largely refracted by the cornea 91 and passes through the pupil 92, the range of view of a person lies within the range of the diameter of the pupil 92. That is, a visible range Q shown in FIG. 4 corresponds to the area of formation of the image on the retina 93. When viewing the object X via the first color bar 321 formed on the surface of the dummy lens 10, a part of the visibility within the visible range Q is blocked by the first color bar 321. This blocked range is referred to as a blocked range S. As illustrated in FIG. 4, the blocked range S varies according to the width of the first color bar 321. For visually recognizing the object X via the first color bar 321, the width of the first color bar 321 needs to be smaller than the diameter of the pupil 92. In this arrangement, a visually recognizable area remains even when a part of the visibility is blocked by the blocked range S, and allows the object X to be visually recognized.

Figure 5:
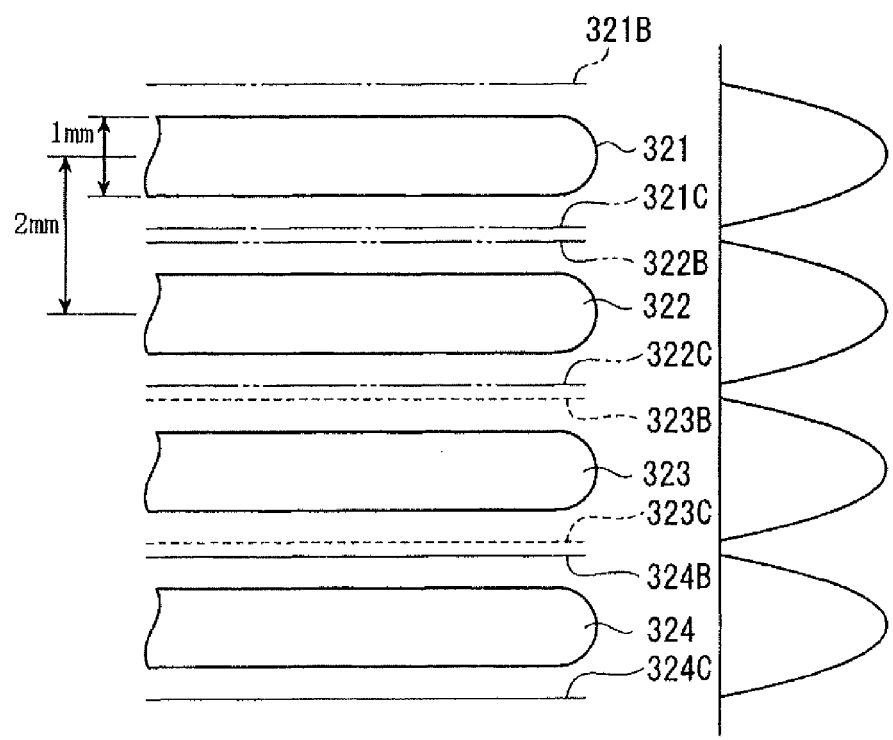
FIG. 5 illustrates a condition of color bars practically viewed by a wearer wearing spectacles according to the first embodiment.

The color bars actually viewed during the measurement of the vision shift amount of the wearer practically wearing the spectacles are now explained. In the condition of near view, the wearer wearing the spectacles 100 views the first color bar 321, the second color bar 322, the third color bar 323, and the fourth color bar 324 in blurring conditions with larger widths of the lines than the actual widths (modulated color conditions due to the effect of out-of-focus condition or diffraction). FIG. 5 schematically illustrates a light absorption spectrum in the peripheral areas of the four color bars. According to this light absorption spectrum, the absorption becomes the maximum at each center of the first color bar 321, the second color bar 322, the third color bar 323, and the fourth color bar 324 in the width direction, and decreases in the direction away from the respective color bars. That is, the gradation becomes lighter in the direction of shifting away from the respective color bars. The gradation of the first color bar 321 ends on a first boundary line 321B and on a second boundary line 3210, The gradation of the second color bar 322 ends on a third boundary line 322B and on a fourth boundary line 322C, The gradation of the third color bar 323 ends on a fifth boundary line 323B and on a sixth boundary line 323C. The gradation of the fourth color bar 324 ends on a seventh boundary line 324B and on an eighth boundary line 324C. In this case, a new white line is visible between the second boundary line 3210 and the third boundary line 322B (transmission light). Similarly, a new white line is visible between the fourth boundary line 322C and the fifth boundary line 323B and between the sixth boundary line 323C and the seventh boundary line 324B (transmission light). That is, a larger number of lines than the actual number of the formed color bars can be seen.

Figure 6:
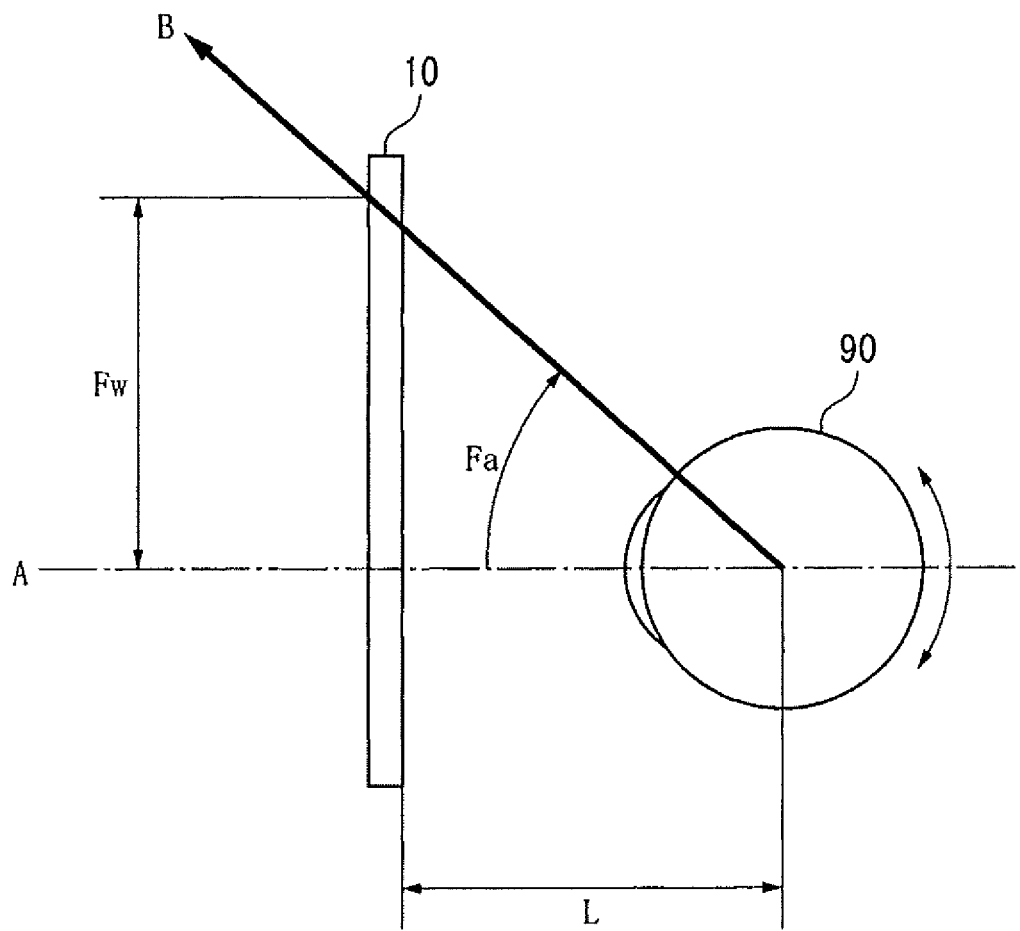
FIG. 6 illustrates a method of measuring a side view amount according to the first embodiment.

A method of obtaining the side view amount by using the second determination mark 33 is now explained. As illustrated in FIG. 6, the eyeball 90 viewing a side B after viewing in a front direction A is discussed. According to this method, an equation (1) shown below holds, in which: the distance between the eyeball 90 and the dummy lens 10 (spectacle wearing distance) is L; the angle formed by the front direction A and the side B (horizontal visible field angle) is Fa; and the distance between the position on the dummy lens 10 through which the vision passes while viewing in the front direction A and the position on the dummy lens 10 through which the vision passes while viewing the side B is Fw (horizontal view field width). In this case, the horizontal view field angle can be calculated by measuring the horizontal view field width Fw as the side visible amount using the method according to this embodiment of the invention and applying the measured value to the equation (1).

$$Fa = \tan^{-1}(Fw/L) \qquad (1)$$

1-2. Structure of Vision Shift Amount Measuring Jig

A vision shift amount measuring jig which forms the reference mark 31, the first determination mark 32, and the second determination mark 33 on the dummy lens 10 is now explained.

Figure 7A:
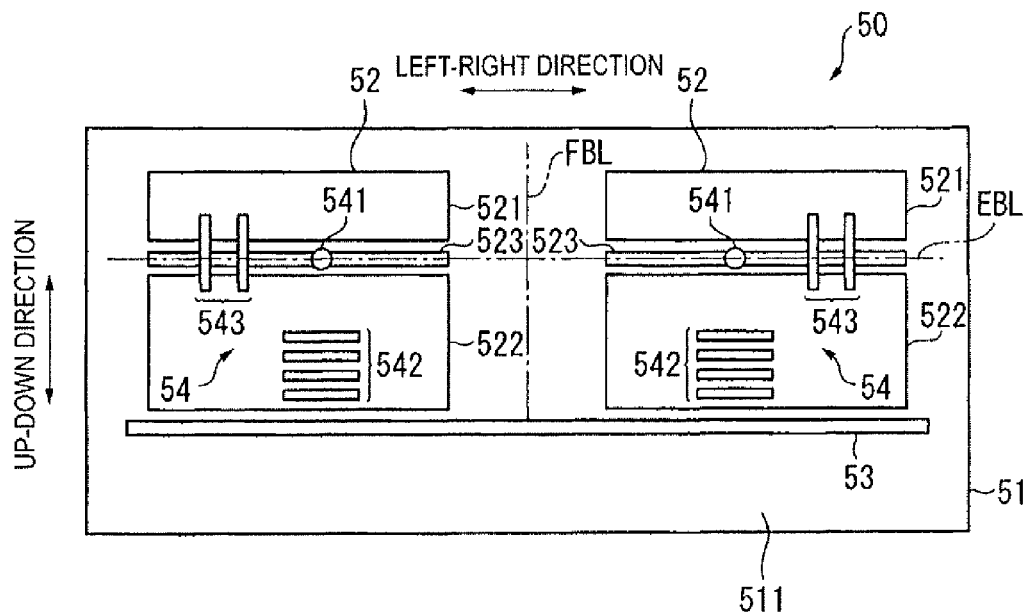
Figure 7B:
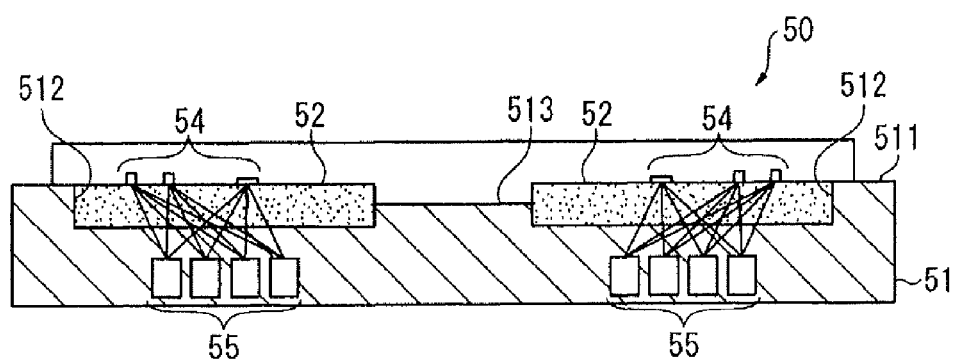

As illustrated in FIGS. 7A and 7B, a measuring jig 50 includes a rectangular parallelepiped spectacle holding stand 51 for holding the spectacles 100, a pair of lens carrying units 52 disposed at positions opposed to the two dummy lenses 10 of the spectacles 100 held on the upper surface of the spectacle holding stand 51, a frame supporting member 53 for adjusting the position of the spectacles 100, and a stamp forming unit 54 for forming the reference mark 31, the first determination mark 32, and the second determination mark 33.

The spectacle holding stand 51 has a carrying surface 511 as the upper surface opposed to the dummy lenses 10 when the spectacles 100 are placed on the spectacle holding stand 51. The carrying surface 511 has a pair of rectangular concave portions 512 capable of accommodating the lens carrying units 52 at positions opposed to the dummy lenses 10, and an intermediate portion 513 in an area sandwiched between the pair of the concave portions 512 and having an upper surface at a position lower than the height of the carrying surface 511. A frame reference line FEL extending in the up-down direction in FIG. 7A is formed at the center of the intermediate portion 513. In placing the spectacles 100, the center of the bridge 22 of the spectacle frame 20 is aligned with the frame reference line FEL.

Each of the lens carrying units 52 is provided within the corresponding one of the pair of the concave portions 512. Each of the lens carrying units 52 has a carrying upper portion 521 and a carrying lower portion 522 whose boundary corresponds to a distance eye point reference line EBL indicating a distance eye point line FL, and a groove 523 formed between the carrying upper portion 521 and the carrying lower portion 522. The carrying upper portion 521 and the carrying lower portion 522 are made of rectangular low-repulsive elastic materials capable of being accommodated within the concave portions 512. It is preferable that the low-repulsive elastic materials have appropriate elasticity for avoiding damage to the surface of the dummy lens 10, such as urethane. The groove 523 is provided in a concave shape on the carrying surface 511 of the spectacle holding stand 51 along the distance eye point reference line EBL. The groove 523 is formed in such a manner as to allow a distance eye point reference point 541 of the stamp forming unit 54 described later to move along the groove 523.

The frame supporting member 53 is a long component extending in parallel with the distance eye point reference line EBL, and is freely movable in the up-down direction (direction crossing the distance eye point reference line EBL at right angles) in FIG. 7A. The frame supporting member 53 adjusts the position of the spectacles 100 by shifting while contacting the lower sides of the frames 21. The frame supporting member 53 can be manually controlled.

Each of the stamp forming units 54 is provided on the corresponding lens carrying unit 52 as a group of projections disposed at positions corresponding to the reference mark 31, the first determination mark 32, and the second determination mark 33 formed on the surface of the dummy lens 10. More specifically, each of the stamp forming units 54 has the distance eye point reference point 541, a first projection 542 corresponding to the first determination mark 32, and a second projection 543 corresponding to the second determination mark 33.

The distance eye point reference point 541 is a cylindrical projection whose one end engages with the groove 523 in such a manner as to slide along the groove 523.

The first projection 542 has four projection bars corresponding to the first color bar 321, the second color bar 322, the third color bar 323, and the fourth color bar 324 described above. These four projection bars extend in parallel with the distance eye point reference line EBL with each clearance between the adjoining projection bars set at a predetermined length. This predetermined space is equivalent to each space between the color bars described above. The four projection bars are affixed to the surface of the carrying lower portion 522 of the lens carrying unit 52.

The second projection 543 has two projection bars corresponding to the fifth color bar 331 and the sixth color bar 332 described above. These two projection bars are disposed in the direction crossing the distance eye point reference line EBL at right angles with a predetermined space between the projection bars. This predetermined space is equivalent to the distance between the fifth color bar 331 and the sixth color bar 332. Each of the two projection bars has an engaging portion (not shown) capable of engaging with the groove 523. These engaging portions engage with the groove 523 in such a manner as to slide along the groove 523.

A connection portion (not shown) for connecting one end of each of the engaging portions and one end of the distance eye point reference point 541 is provided within the groove 523. Thus, the distance eye point reference point 541 and the second projection 543 move with each other on the distance eye point reference line EBL. Thus, the distance between the distance eye point reference point 541 and each of the projection bars included in the second projection 543 is kept constant. This distance is equivalent to the distance between the reference mark 31 and each of the color bars.

The spectacle holding stand 51 contains ink tanks 55 in respective colors communicating with the groups of projections such that ink can be supplied to the groups of projections as necessary.

1-3. Vision Shift Amount Measuring Method

A method of forming the marks on the dummy lenses 10 by using the measuring jig 50 and measuring the vision shift amount is now explained.

1-3-1. Mark Forming Step

Initially, the frame supporting member 53 is positioned. The spectacle frame 20 is opened, and the spectacles 100 are placed on the lens carrying units 52 in such a direction that the outer surfaces of the dummy lenses 10 contact the lens carrying units 52. In this case, the spectacles 100 are placed such that the center of the spectacle frame 20 agrees with the frame reference line FBL. The distance eye point is determined for each of the dummy lenses 10 in advance, and the mark is attached to this position. Thus, the position of the spectacles 100 is finely adjusted with the frame supporting member 53 contacting the frames 21 such that the distance eye point of the dummy lens 10 and the distance eye point reference line EBL agree with each other.

In this case, positional fine adjustment is performed such that the distance eye point of the dummy lens 10 agrees with the distance eye point reference point 541 by moving the distance eye point reference point 541.

After the distance eye point reference point 541 and the frame supporting member 53 are positioned, the outer surfaces of the pair of the dummy lenses 10 are pressed against the low-repulsive materials of the pair of the lens carrying units 52 without changing the determined positions. By the press of the dummy lenses 10 against the stamp forming units 54, ink is charged to the groups of the projection bars, and the reference mark 31, the first determination mark 32, and the second determination mark 33 are formed on each surface of the dummy lenses 10.

By this step, the dummy lenses 10 having the marks shown in FIG. 1 are produced, and a condition for measuring the vision shift amount is now prepared.

1-3-2. Measuring Step

A measuring step for measuring the vision shift amount is herein explained.

The wearer wears the spectacles 100 to which the dummy lenses 10 having the marks are attached, and initially checks the positions of the visions both in the distant view and near view for measurement of the eyeball downward movement amount.

Figure 8A:
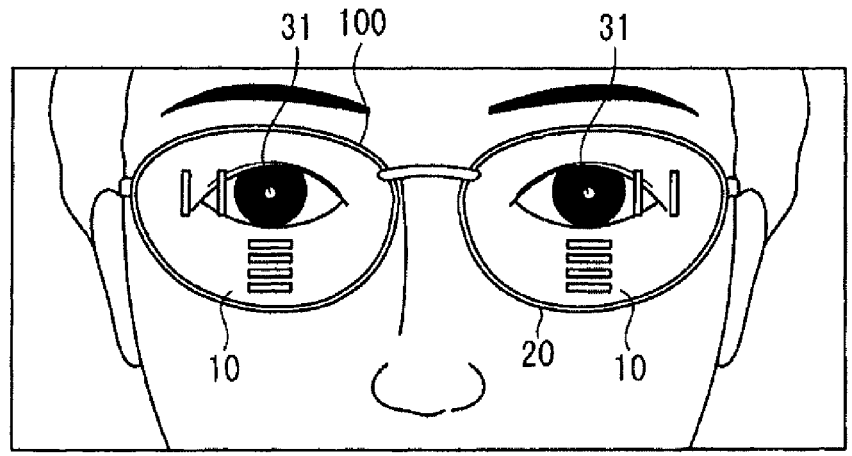
Figure 8B:
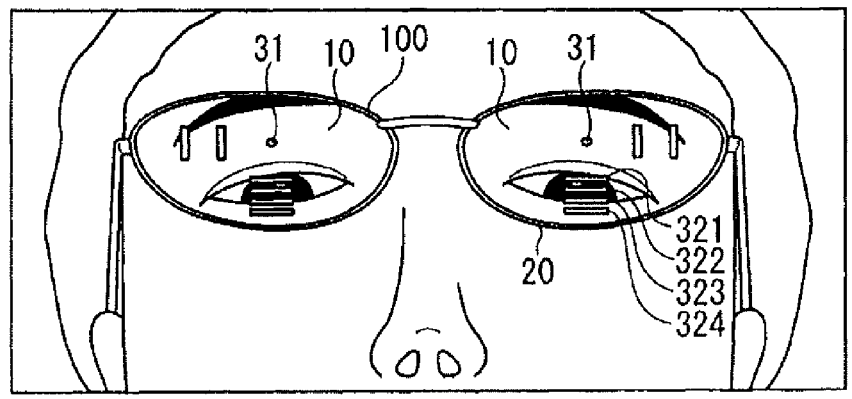

More specifically, whether the pupil center (vision) of the wearer wearing the spectacles 100 in the front view condition passes through the reference mark 31 is checked (checking step, see FIG. 8A). Then, which position of the first determination mark 32 the pupil center (vision) of the wearer wearing the spectacles 100 in the condition of reading a book (near view) passes through is checked (determining step, see FIG. 8B), In this embodiment, the first determination mark 32 is constituted by the four color bars of the first color bar 321 (black), the second color bar 322 (green), the third color bar 323 (red), and the fourth color bar 324 (blue). Thus, the wearer determines the color closest to the position through which the vision of the wearer passes. Since the new white lines are recognized between the respective color bars in this embodiment, the wearer may select one of the white lines.

The vision position of the near view is determined by these steps, In this case, the distance between the reference mark 31 and the selected color bar or white line corresponds to the eyeball downward movement amount of the wearer.

Next, the position of the vision in the side view is checked for measuring the side view amount of the wearer.

Figure 8C:
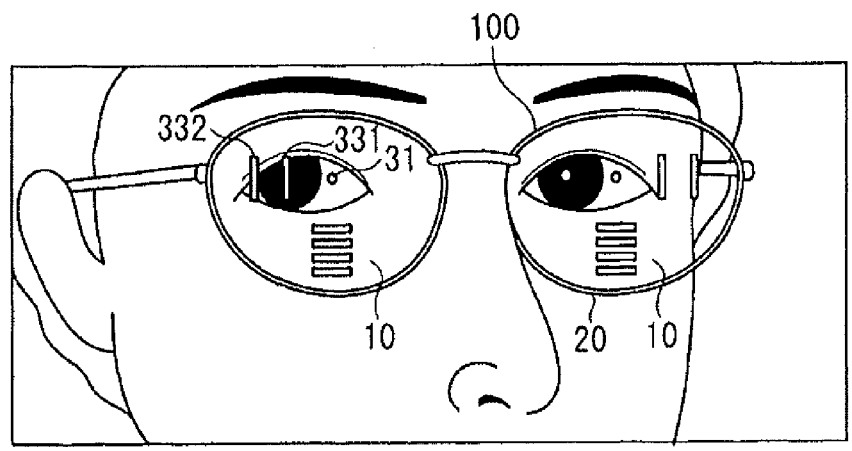

More specifically, which position of the second determination mark 33 the pupil center (vision) of the wearer wearing the spectacles 100 in the side view passes is checked (determining step, see FIG. 8C). In this embodiment, the second determination mark 33 is constituted by the two color bars of the fifth color bar 331 (black) and the sixth color bar 332 (red). Thus, the wearer determines the color bar having the color closest to the position through which the vision of the wearer passes. Since the new white lines are recognized between the respective color bars in this embodiment, the wearer may select one of the white lines.

The vision position of the side view is determined by these steps. In this case, the distance between the reference mark 31 and the selected color bar or white line corresponds to the side view amount of the wearer.

1-4. Operational Advantages of First Embodiment

According to the first embodiment, the following operational advantages can be offered.

In this embodiment, the eyeball downward movement amount is obtained by determining the position of the near eye point based on the first determination mark 32 constituted by the plural color bars under the condition in which the dummy lenses 10 having the respective marks are attached to the spectacle frame 20 practically worn by the wearer. In addition, the side view amount is obtained by determining the position of the vision in the side view based on the second determination mark 33 constituted by the plural color bars.

Since the measurement is performed while the wearer is wearing the spectacles having the dummy lenses 10 attached to the spectacle frame 20 practically worn by the wearer, not only the head and eyeball movements of the wearer (viewing action) but also the posture of the wearer are taken into consideration during measurement. As a result, the vision shift amount optimized for each person can be highly accurately measured.

The first determination mark 32 constituted by the plural opaque color bars are formed in the area expected to contain the near eye point. In the near view of the wearer practically wearing the spectacles, the color bars on the dummy lenses 10 are recognized as blurred bars. In this case, visual recognizability of colors lowers. According to this embodiment, however, the color bars formed as opaque color bars have a high rate of light reflection. Thus, the amount of light entering the eyes increases, which allows secure determination of the color difference (improvement of visual recognizability). Accordingly, the wearer can easily determine the color when measuring the vision shift amount.

The plural color bars are disposed with the predetermined spaces between the respective color bars (2 mm for each distance between the center lines). Thus, the wearer can see an object through the spaces between the color bars. In addition, the width of each color bar is set at 1 mm as a width sufficiently smaller than the size of a human pupil (2 mm or longer) such that the wearer can see the object. Thus, the measurement can be performed in the near view closer to the natural condition, which improves the measurement accuracy.

According to this embodiment, the position of the distance eye point of the dummy lens 10 is determined for each of the wearers, and the reference mark 31 is formed at this position. Moreover, the first determination mark 32 constituted by the plural color bars is formed in the area expected to contain the near eye point. Thus, in measuring the eyeball downward movement amount, the wearer is only required to determine the position of the near eye point. That is, the wearer determines which color of the plural color bars of the first determination mark 32 can be seen in the near view.

According to this method, the distance eye point is fixed, and only the near eye point is determined. In this case, the eyeball downward movement amount is calculated based on the absolute position. Thus, the operation can be simplified, and the measurement can be performed with high accuracy.

Each of the first determination mark 32 and the second determination mark 33 is constituted by the plural lines having different colors. Thus, these lines can be easily recognized by the wearer, and the measurement can be carried out without imposing a burden on the wearer.

Accordingly, the measurement can be easily executed by a person in a shop or the like who does not have special techniques.

According to this embodiment, various types of marks are formed on each surface of the dummy lenses 10 by using the measuring jig 50. Since the stamp forming unit 54 is provided on the upper surface of the lens carrying unit 52, the reference mark 31, the first determination mark 32, and the second determination mark 33 can be easily formed on the dummy lens 10 only by pressing the dummy lens 10 against the stamp forming unit 54.

Particularly, since the lens carrying unit 52 is made of low-repulsive material, the group of projections of the stamp forming unit 54 closely contact the surface of the dummy lens 10 when the dummy lens 10 is pressed against the stamp forming unit 54. Thus, ink can be securely attached to the surface of the dummy lens 10.

The measuring jig 50 has the movable type distance eye point reference point 541 which can deal with various distance eye points different for each wearer. Thus, lens design corresponding to the viewing action of each wearer becomes highly accurate.

The second determination mark 33 moves with the distance eye point reference point 541. Thus, the distance between the distance eye point and the second determination mark 33 can be kept constant. In this case, the necessity for adjusting the position of the second determination mark 33 in accordance with the position shift of the distance eye point is eliminated, which improves maneuverability.

The measuring jig 50 has the ink tank 55 for supplying ink in respective colors to the group of projections of the stamp forming unit 54. Particularly in the structure which charges ink when the group of projections are pressed by a predetermined force, no special operation is required for ink charge, which provides preferable maneuverability.

Accordingly, even a person in a shop or the like who does not have special techniques can easily form the reference mark 31, the first determination mark 32, and the second determination mark 33 on each surface of the dummy lenses 10 by using the measuring jig 50, and can easily perform measurement.

2. Second Embodiment

The structure in a second embodiment is similar to that in the first embodiment except that a stamp member is used as a vision shift amount measuring jig. Thus, the vision shift amount measuring jig in this embodiment is hereinafter explained.

2-1. Structure of Vision Shift Amount Measuring Jig

Figure 9A:
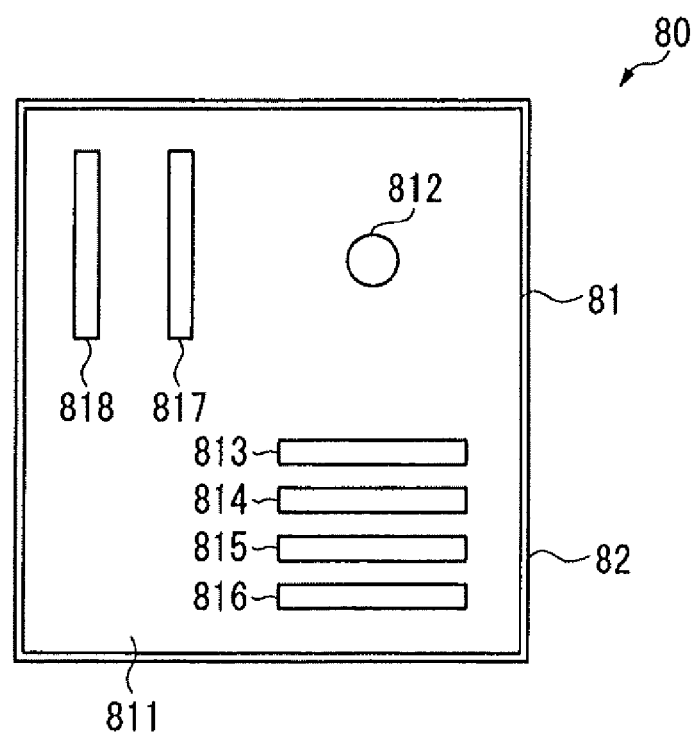
Figure 9B:
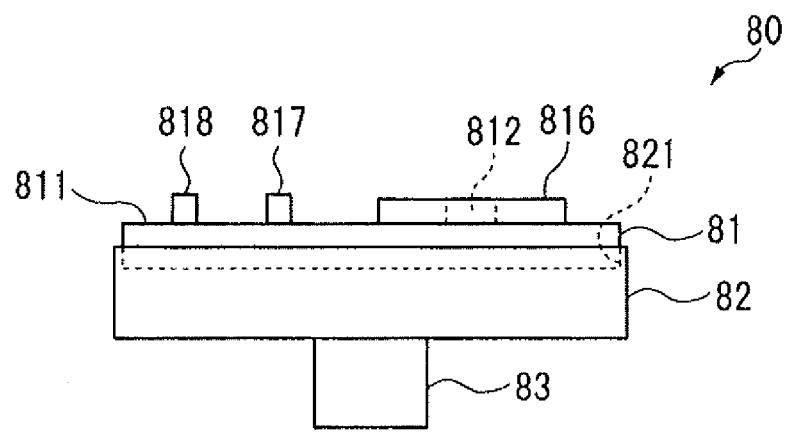

As illustrated in FIGS. 9A and 9B, a stamp member 80 includes a pressing portion 81 to be pressed against an object, a pedestal portion 82 supporting the pressing portion 81, and a holding portion 83 as a convex part disposed on the surface of the pedestal portion 82 opposite to the pressing portion 81 side.

The pressing portion 81 has a pressing surface 811 opposed to the object, from which surface 811 a plurality of projections protrude in convex shapes. The projections are located at positions corresponding to the reference mark 31, the first determination mark 32, and the second determination mark 33 described above. More specifically, a cylindrical reference projection 812 is provided at the position corresponding to the reference mark 31, rectangular parallelepiped first projection 813, second projection 814, third projection 815, and fourth projection 816 are provided at the positions corresponding to the plural color bars constituting the first determination mark 32. Moreover, rectangular parallelepiped fifth projection 817, sixth projection 818 are provided at the positions corresponding to the plural color bars constituting the second determination mark 33. These projections communicate with ink tanks (not shown) accommodated within the pedestal portion 82 as components made of materials allowing penetration of ink supplied from the ink tanks.

The pedestal portion 82 has a concave 821 for accommodating the pressing portion 81, and the not-shown ink tanks.

The pressing portion 81 is accommodated in the concave 821 in such a manner as to slide therein, and switches between a full-withdrawal condition in the concave 821 and a projecting condition in which the pressing portion 81 projects from the concave 821 while held thereon (see FIG. 9B). More specifically, the pressing portion 81 projects from the concave 821 while held in the normal condition, but is completely withdrawn into the concave 821 when a predetermined force is applied to the pressing surface 811 (projections) for pressing the pressing surface 811 against the object. The ink tanks initiate charging ink to the respective projections at the time when the pressing portion 81 is completely withdrawn into the concave 821.

The holding portion 83 is a convex part formed approximately at the center of the surface of the pedestal portion 82 opposite to the pressing portion 81 side. The holding portion 83 is held when the stamp member 80 is moved.

According to this structure, the pressing surface 811 of the stamp member 80 is pressed against the surface of the dummy lens 10 to form the reference mark 31, the first determination mark 32, and the second determination mark 33 shown in FIG. 1.

Then, the vision shift amount is measured by using the dummy lens 10 having the marks thus formed similarly to the first embodiment.

2-2. Operational Advantages of Second Embodiment

According to the second embodiment, the following operational advantages can be offered by using the stamp member 80. The operational advantages provided by the dummy lens 10 having the respective marks are similar to those in the first embodiment.

In the second embodiment, the respective marks can be formed on each surface of the dummy lenses 10 only by the easy operation of pressing the pressing surface 811 of the stamp member 80 against the surface of the dummy lens 10. In this case, the necessity for using a special device is eliminated, and thus the measurement can be performed at low cost.

3. Third Embodiment

According to a third embodiment, a method of measuring (checking) the vision shift amount by using spectacles having progressive-power lenses attached to the spectacle frame practically worn by the wearer will be discussed. In the third embodiment, the spectacle lenses are designed based on the vision shift amount measured in the first embodiment, and then whether the designed spectacle lenses are appropriate for the wearer is checked.

3-1. Spectacle Lens

Figure 10:
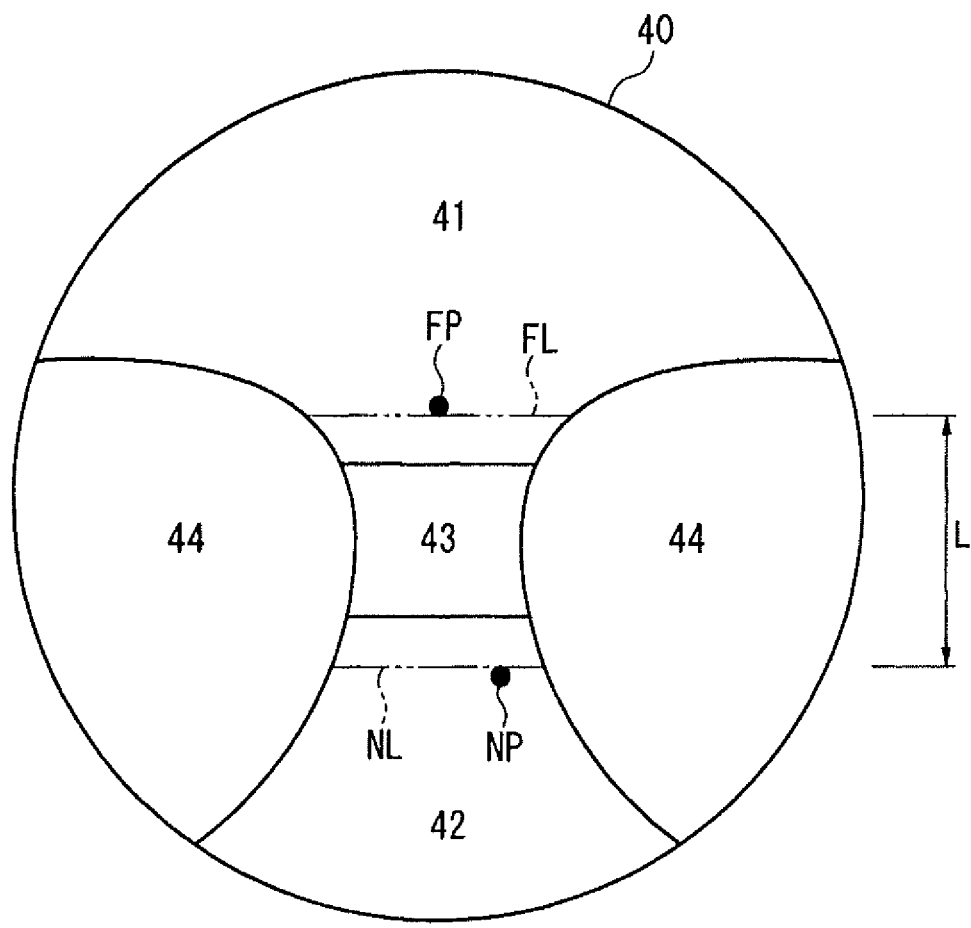
FIG. 10 schematically illustrates a progressive-power lens on which marks are formed by a vision shift amount measuring method according to a third embodiment of the invention.

As illustrated in FIG. 10, a progressive-power lens formed into a spectacle lens 40 has a distance portion 41 located in the upper region, a near portion 42 located in the lower region, and a progressive band 43 located between the distance portion 41 and the near portion 42, and side portions 44 as aberration portions disposed adjacent to both sides of the progressive band 43.

The distance portion 41 has relatively low plus power as average power to be appropriate for distance view. Particularly, the position through which the horizontal line passing through the pupil center (i.e., the vision) passes in the front view of the wearer is referred to as a distance eye point FP, and a line passing through the distance eye point FP and extending in the left-right direction is referred to as the distance eye point line FL.

The near portion 42 has a relatively high plus power as average power to be appropriate for near view (for reading, for example). Particularly, the position through which the vision passes in the near view (i.e., downward view) of the wearer is referred to as a near eye point NP, and a line passing through the near eye point NP and extending in the left-right direction is referred to as a near eye point line NL.

The progressive band 43 is an area where a relative plus average addition power progressively varies between the distance portion 41 and the near portion 42.

The side portions 44 are areas called astigmatism areas. Since an object is recognized as a doubled shape when viewed through the side portions 44, the wearer does not generally use the side portions for viewing an object.

Figure 11:
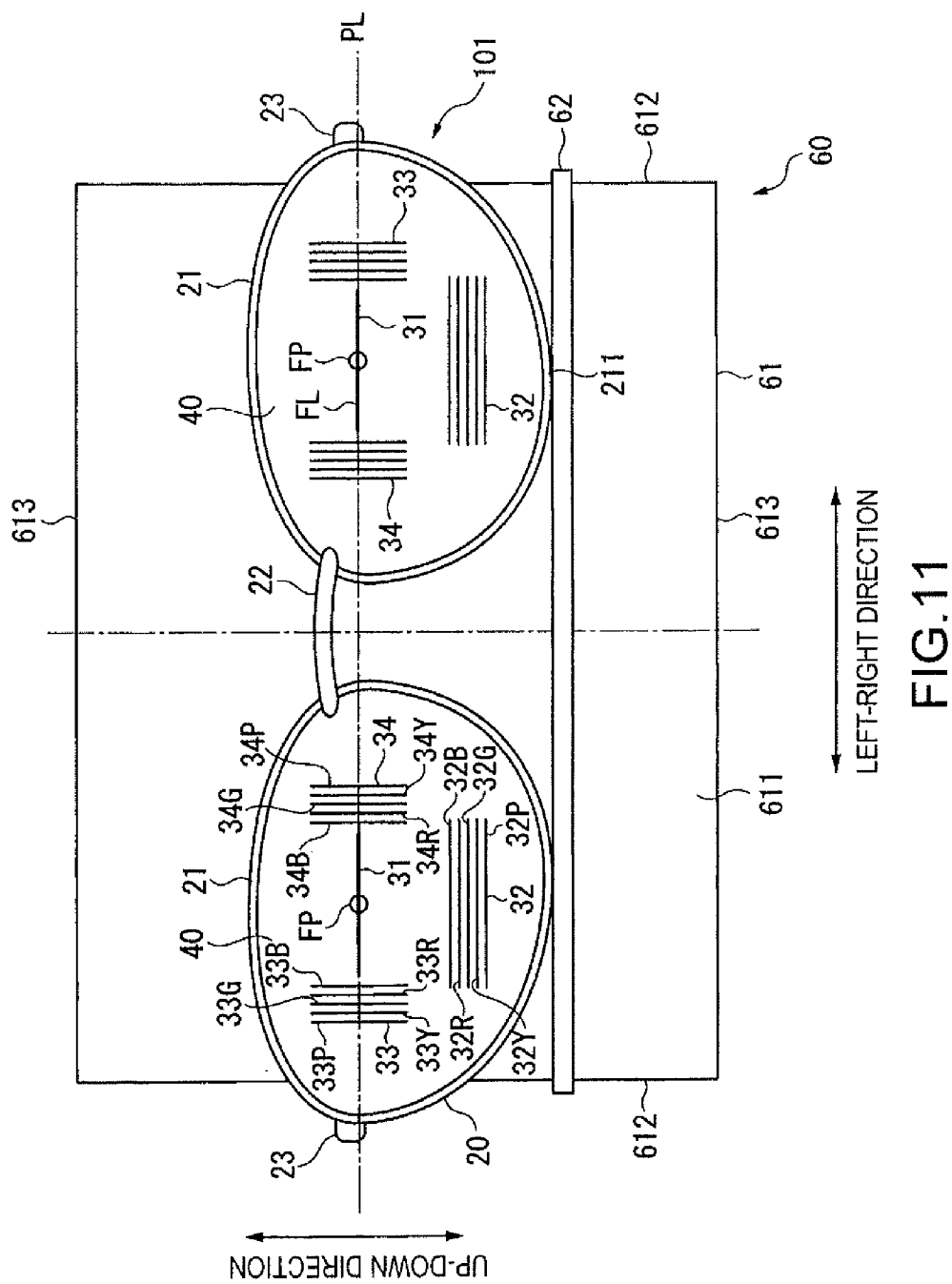
FIG. 11 is a plan view illustrating a condition in which the marks are formed on spectacle lenses according to the third embodiment.

The spectacle lenses 40 are produced by molding the progressive-power lenses having this structure, and are attached to the spectacle frame 20 to become spectacles 101 (see FIG. 11).

Marks formed on the surface of each of the spectacle lenses 40 are now explained.

As illustrated in FIG. 11, each of the spectacle lenses 40 has the reference mark 31 indicating the distance eye point FP, the first determination mark 32 formed in the area expected to contain the near eye point, the second determination mark 33 constituting one end of a horizontal visible field passing through the distance eye point and extending in the left-right direction of the spectacle lens 40, and a third determination mark 34 constituting the other end of the horizontal visible field.

The reference mark 31 is the distance eye point line FL which passes the distance eye point FP indicating the position of the distance eye point and extends linearly in the left-right direction of the spectacle lens 40. The distance eye point FP is the position through which the vision passes in the horizontal view of the wearer practically wearing the spectacles 101, and is determined in advance.

The first determination mark 32 is formed in the area expected to contain the near eye point NP (the near portion 42 in FIG. 10), and is constituted by a plurality of lines extending in parallel with the distance eye point line FL. These plural lines have colors different from each other. similarly to the first embodiment, the first determination mark 32 has five lines of a line 32B (black), a line 32R (red), a line 32G (green), a line 32Y (yellow), a line 32P (purple) in this order from the distance eye point FP side.

The second determination mark 33 is constituted by a plurality of lines formed at the outside one end of the horizontal visible field of the spectacle lens 40. These plural lines extend linearly in the direction crossing the distance eye point line FL at right angles, and are constituted by five lines of a line 33B (black), a line 33R (red), a line 33G (green), a line 33Y (yellow), and a line 33P (purple) in this order from the center of the spectacle lens 40.

The third determination mark 34 is constituted by a plurality of lines formed at the inside one end of the horizontal visible field of the spectacle lens 40. These plural lines extend linearly in the direction crossing the distance eye point line FL at right angles, and are constituted by five lines of a line 34B (black), a line 34R (red), a line 34O (green), a line 34Y (yellow), and a line 34P (purple) in this order from the center of the spectacle lens 40.

Each of the plural lines constituting the first determination mark 32, the second determination mark 33, and the third determination mark 34 has an equal width of 0.5 mm. The plural lines are disposed such that each distance between the centers of the lines in the width direction becomes 1.5 mm.

3-2. Mark Forming Method

A method of forming the reference mark 31, the first determination mark 32, the second determination mark 33, and the third determination mark 34 on each surface of the spectacle lenses 40 is now explained.

Figure 12:
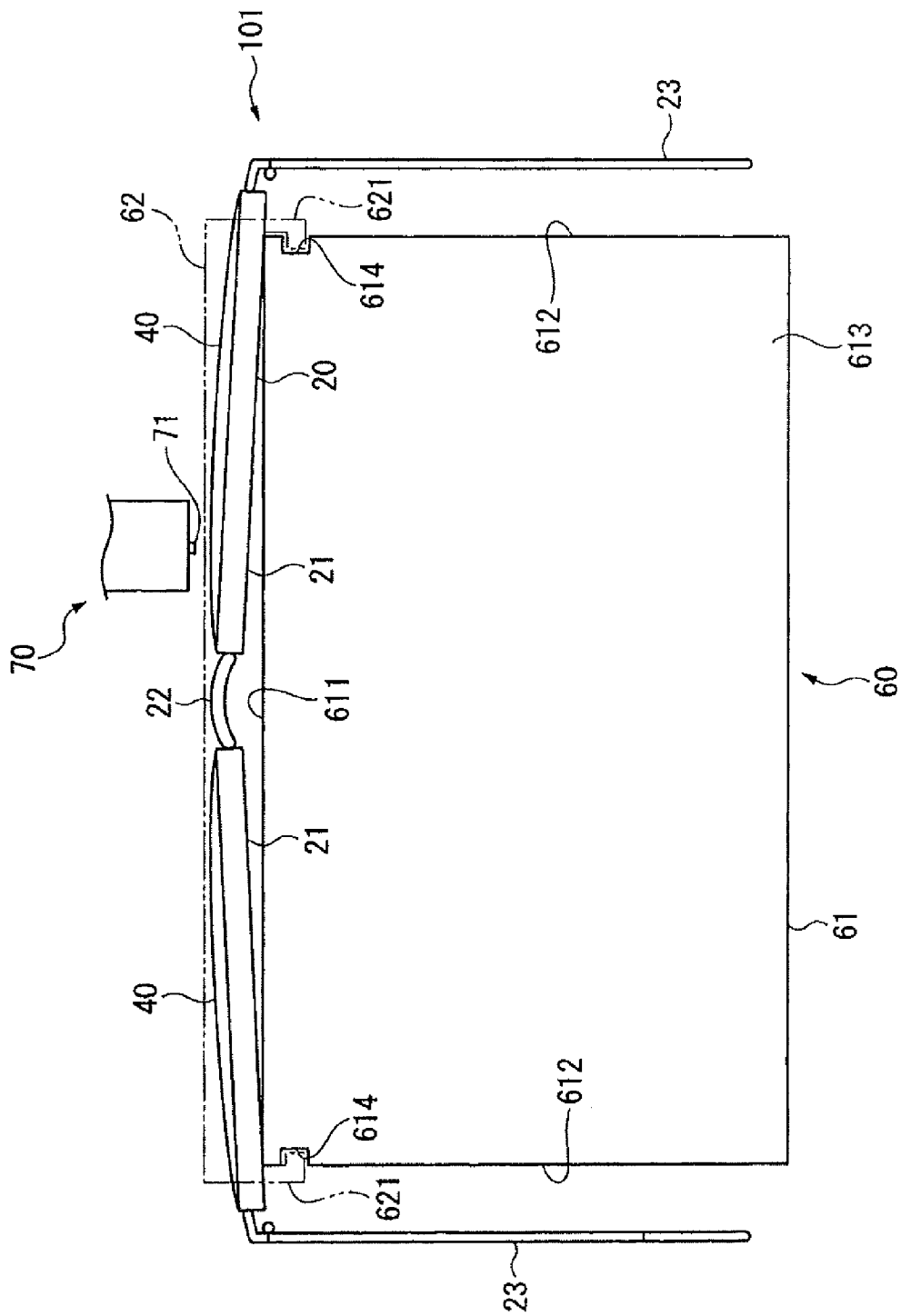
FIG. 12 is a front view illustrating a condition of forming the marks on the spectacle lenses by using ink jet according to the third embodiment.

Initially, as illustrated in FIGS. 11 and 12, the spectacles 101 practically worn by the wearer are placed on a carrying stand 60.

The carrying stand 60 has a rectangular parallelepiped base 61 having a carrying surface 611 as the upper surface opposed to the spectacle lenses 40 when the spectacles 101 are placed on the carrying stand 60, and a frame supporting member 62 provided in such a manner as to freely move in one direction along the carrying surface 611 of the base 61 to support the spectacles 101 at an appropriate position.

The base 61 has a pair of first side portions 612 standing on the carrying surface 611 in the vertical direction and disposed opposed to each other, and another pair of second side portions 613 disposed opposed to each other. While the spectacles 101 are being placed, the frame 21 to which the spectacle lenses 40 are attached are carried on the carrying surface 611 with the outer surfaces of the spectacle lenses 40 facing upward, and the left and right temples 23 are located along the opposed first side portions 612. The carrying surface 611 has a flat shape, and the spectacles 101 placed on the carrying surface 611 can move in one direction along the carrying surface 611.

Notches 614 as recessed portions are linearly formed on the upper parts of the first side portions 612, that is, in the vicinity of the carrying surface 611 to extend in parallel with the carrying surface 611.

The frame supporting member 62 is a long component having a length equal to or larger than each length of the second side portions 613 in the left-right direction. Engaging portions 621 bended in U shapes (hook shapes) are provided at both ends of the frame supporting member 62. Both tips of the engaging portions 621 engage with the notches 614 of the base 61 to freely move in the up-down direction of the spectacle lenses 40. The frame supporting member 62 controls the position of the spectacles 101 by contacting lower sides 211 of the frames 21 and moving. The distance eye point FP of each of the spectacle lenses 40 can be aligned with a positioning line PL on the carrying surface 611 by using a detection unit provided for detecting the condition that the distance eye point FP comes to the positioning line PL.

When the spectacles 101 are placed on the carrying stand 60, the frame supporting member 62 moves by the operation of a not-shown control unit, and stops when the detection unit detects the position where the distance eye point line FL of each of the spectacle lenses 40 agrees with the positioning line PL of the carrying surface 611.

Then, the reference mark 31, the first determination mark 32, the second determination mark 33, and the third determination mark 34 are formed by an ink jet method. As illustrated in FIG. 12, ink is jetted from a nozzle 71 of an ink jet head 70 to directly print the reference mark 31, the first determination mark 32, the second determination mark 33, and the third determination mark 34 on the spectacle lens 40 (mark forming step).

3-3. Vision Shift Amount Measuring Method

In this embodiment, the eyeball downward movement amount, and the eyeball inward movement amount and the eyeball outward movement amount (side view amounts) defined by the horizontal visible field are measured as the vision shift amounts.

Initially, the method of measuring the eyeball downward movement amount is explained.

The wearer wears the spectacles 101 on each of which the reference mark 31, the first determination mark 32, the second determination mark 33, and the third determination mark 34 are formed, and initially checks whether the vision in the horizontal view agrees with the distance eye point FP. When the vision does not agree with the distance eye point FP, the position of the distance eye point is again adjusted.

Then, the wearer selects the line closest to the position (near eye point NP) through which the vision in the near view (in reading, for example) passes from the plural lines of the first determination mark 32 (determining step). Since the plural lines have corresponding different colors, the wearer is only required to answer the name of the selected color. When the color of the line closest to the near eye point NP is green, the distance between the distance eye point line FL as the reference mark 31 and the line 32G corresponds to a length L of the eyeball downward movement amount.

Next, a method of obtaining the horizontal visible field by measuring the eyeball inward movement amount and the eyeball outward movement amount (side view amounts) is explained.

The wearer determines until which line of the plural lines of the second determination mark 33 formed on each of the spectacle lenses 40 the wearer can recognize. The distance between the determined line and the distance eye point corresponds to the eyeball outward movement amount (side view amount). Also, the wearer determines until which line of the plural lines of the third determination mark 34 formed on each of the spectacle lenses 40 the wearer can recognize. The distance between the determined line and the distance eye point corresponds to the eyeball inward movement amount. In this case, the distance between the determined lines corresponds to the horizontal visible field. More specifically, when it is determined that the wearer can see until the red line 33R of the second determination mark 33 and until the yellow line 34Y of the third determination mark 34, the distance between the line 33R and the line 34Y corresponds to the horizontal visible field.

3-4. Operational Advantages of Third Embodiment

According to the third embodiment, the following operational advantages can be offered.

In the third embodiment, the reference mark 31 and the first determination mark 32 are formed on each of the spectacle lenses 40, and the spectacle lenses 40 are attached to the spectacle frame 20 practically worn by the wearer to perform measurement of the vision shift amount.

In this case, the measurement is carried out under the condition in which the wearer is wearing the spectacle frame practically used by the wearer. Thus, not only the head and eyeball movements (viewing action) but also the posture of the wearer are considered in the measurement. Accordingly, the vision shift amount optimized for each person can be measured highly accurately.

In the third embodiment, the second determination mark 33 and the third determination mark 34 are further provided on each of the spectacle lenses 40 to measure the length of the horizontal visible field (vision shift amount).

In this case, the measurement is carried out under the condition in which the wearer is wearing the spectacle frame practically used by the wearer. Thus, the measurement result corresponding to the viewing movement and the posture of the wearer while viewing an object can be obtained. Accordingly, the horizontal visible field (vision shift amount) optimized for each person can be measured highly accurately.

In the third embodiment, the first determination mark 32 is constituted by the plural lines having different colors. Thus, the position of the near eye point NP can be accurately determined through selection from the plural choices.

Similarly, each of the second determination mark 33 and the third determination mark 34 is constituted by the plural lines having different colors. Thus, the ends of the horizontal visible field can be accurately determined through selection from the plural choices.

The wearer only required to determine the visible colors can easily make decision of recognition. Thus, the measurement can be easily performed without imposing a burden on the wearer.

Since each of the first determination mark 32, the second determination mark 33, and the third determination mark 34 is constituted by the plural lines having different colors, the wearer is only required to determine the colors practically recognized during measurement. Thus, the measurement can be easily performed without imposing a burden on the wearer. Accordingly, the measurement can be easily carried out by a person in a shop or the like who does not special techniques, which increases usability.

According to the third embodiment, the reference mark 31, the first determination mark 32, the second determination mark 33, and the third determination mark 34 are provided by directly forming the predetermined patterns on each of the spectacle lenses 40 using the ink jet method. The ink jet method can easily produce fine patterns. Thus, a person executing the measurement can form the marks with ease only by placing the spectacles 101 on the carrying stand 60.

MODIFIED EXAMPLES

The invention is not limited to the embodiments described herein. Obviously, the modifications and improvement of the embodiments are included in the scope of the invention as long as similar advantages can be provided.

Figure 13A:
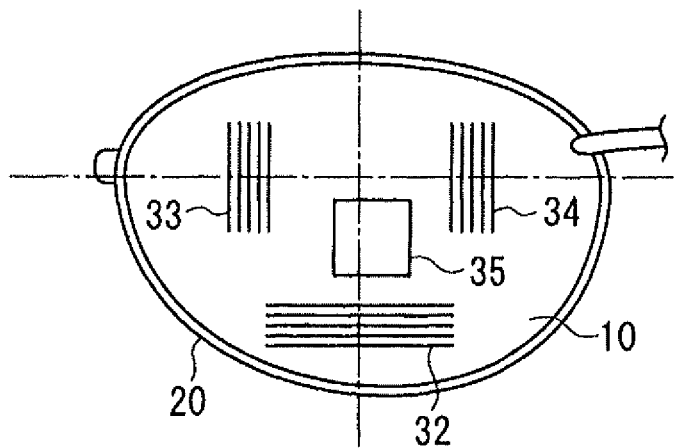

For example, a blind 35 may be provided on an area corresponding to the progressive band of the spectacle lens 40 in the respective embodiments as illustrated in FIG. 13A. The blind 35 is an opaque area, and the wearer cannot see an object through this area.

Since the progressive band of the progressive-lens is not suited for viewing an object, the wearer needs to be trained so as not to see an object through the progressive band. According to this structure, the wearer can easily recognize the position of the area corresponding to the progressive band by using the blind 35. Moreover, the training for not viewing an object through the progressive band (blind 35) can be easily carried out.

Accordingly, the explanation and instructions can be easily given at the time of explaining the progressive-power lens for the wearer in a shop or the like.

Figure 13B:
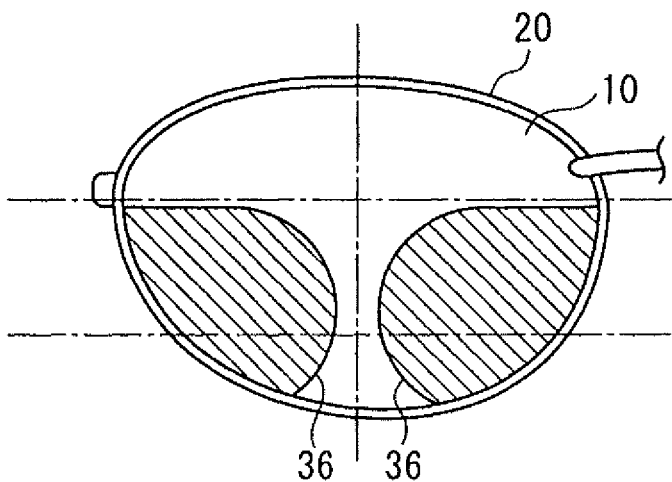

Alternatively, opaque blinds 36 may be provided on areas corresponding to the side portions 44 of the progressive-power lens as illustrated in FIG. 13B. Since the side portions 44 are not suited for viewing an object, the wearer can easily recognize those areas by the existence of the blinds 36. Thus, instructions can be more easily given to a wearer not familiar with the progressive-power lens. Moreover, training for not seeing an object through the side portions 44 can be easily conducted.

A shape as the combination of the modified examples shown in FIGS. 13A and 13B is allowed. The spectacle lenses having this structure facilitate the instructions of the use method of the progressive-power lens given to the wearer.

The method of forming the marks in the first embodiment may be the ink jet method used in the third embodiment, and the method of forming the marks in the third embodiment may be the stamp type method used in the first or second embodiment. The method of forming various marks on the spectacle lens is not limited to those methods but may be other various types of printing methods.

According to the respective embodiments, the marks are formed by directly applying ink to the surface of the dummy lens 10 or the spectacle lens 40. However, these marks may be formed on the surface of a tape to be affixed to the surface of the dummy lens 10 or the spectacle lens 40. In this case, it is important to affix the tape with alignment of the distance eye point of the dummy lens 10 or the spectacle lens 40 and the reference mark formed on the tape.

According to this structure, the tape is only required to be removed at the time of removal of the marks from the dummy lens 10 or the spectacle lens 40. Thus, the process after the measurement is easily carried out. Moreover, according to the method which does not directly apply ink to the lens, requirements for the ink to be used such as easiness of wiping off for removal are eliminated. Thus, cost reduction can be achieved by lowering the cost of ink.

Accordingly, the measuring method according to the invention can be widely used in a spectacle shop or the like as a method for easily measuring a vision shift amount of spectacles.

The entire disclosure of Japanese Patent Application No: 2009-299058, filed Dec. 29, 2009 is expressly incorporated by reference herein.

What is claimed is:

1. A vision shift amount measuring method comprising:
    forming a reference mark indicating a distance eye point on a surface of a spectacle lens attached to a spectacle frame practically worn by a wearer, and forming a plurality of opaque lines in an area expected to contain a shifted vision on the surface of the spectacle lens with a predetermined space between the adjoining lines; and
    allowing the wearer wearing the spectacle frame to select the line closest to a position through which the vision passes from the plural formed lines.
    wherein a vision shift amount comprises an eyeball outward movement produced when an outside of the spectacle lens is viewed by the wearer and an eyeball inward movement produced when an inside of the spectacle lens is viewed by the wearer.

2. The vision shift amount measuring method according to claim 1, wherein the plural lines are disposed such that the distance between the centers of the adjoining lines lies in the range from 1.5mm to 2.5mm.

3. The vision shift amount measuring method according to claim 1, wherein each width of the lines lies in the range from 0.1mm to 1.5mm.

4. The vision shift amount measuring method according to claim 1, wherein at least the adjoining lines of the plural lines have colors different from each other.

5. The vision shift amount measuring method according to claim 1, wherein the plural lines are formed in an area expected to contain a near eye point on the surface of the spectacle lens and disposed in parallel with a horizontal visible field which passes through the distance eye point and extends in the horizontal direction.

6. The vision shift amount measuring method according to claim 1, wherein the plural lines are formed in an area expected to contain one end of a horizontal visible field which passes through the distance eye point and extends in the horizontal direction, and are disposed in the direction crossing the horizontal visible field at right angles.

7. The vision shift amount measuring method according to claim 1, wherein the reference mark and the plural lines are formed by directly applying ink to the spectacle lens using a stamp.

8. The vision shift amount measuring method according to claim 1, wherein the reference mark and the plural lines are formed by directly applying ink to the spectacle lens using an ink jet.

9. The vision shift amount measuring method according to claim 1, wherein the reference mark and the plural lines are formed by producing the reference mark and the plural lines on a surface of a tape capable of adhering to the surface of the spectacle lens, and affixing the tape to the surface of the spectacle lens attached to the spectacle frame practically worn by the wearer with alignment between the distance eye point of the spectacle lens and the reference mark formed on the tape.

10. A vision shift amount measuring jig, comprising:
a spectacle holding stand that holds a spectacle having a spectacle frame to which a spectacle lens is attached, wherein
a lens carrying unit which contains low-repulsive material provided at a position corresponding to the spectacle lens, and a stamp forming unit which contains convex projections disposed at positions corresponding to a reference mark indicating a distance eye point and a plurality of opaque lines provided in an area expected to contain a shifted vision on the surface of the spectacle lens with a predetermined space between the adjoining lines are provided on the upper surface of the spectacle holding stand, and
a vision shift amount comprises an eyeball outward movement produced when an outside of the spectacle lens is viewed by a wearer and an eyeball inward movement produced when an inside of the spectacle lens is viewed by the wearer.

11. The vision shift amount measuring jig according to claim 10, wherein the projection corresponding to the reference mark is provided in such a manner as to freely move in the horizontal direction of the spectacle lens.

12. The vision shift amount measuring jig according to claim 10, further comprising a frame supporting member attached in such a manner as to freely move in the direction crossing the horizontal direction of the spectacle lens at right angles to support the spectacle frame.

* * * * *